(12) United States Patent
Rizq et al.

(10) Patent No.: US 12,128,195 B2
(45) Date of Patent: Oct. 29, 2024

(54) ELECTRONIC CONTROL OF MEDICAL DEVICE DEPLOYMENT SYSTEMS AND METHODS

(71) Applicant: Boston Scientific Scimed, Inc., Maple Grove, MN (US)

(72) Inventors: Raed N. Rizq, Maple Grove, MN (US); Daniel J. Foster, Lino Lakes, MN (US); Ajay Gupta, Shoreview, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 354 days.

(21) Appl. No.: 16/793,290

(22) Filed: Feb. 18, 2020

(65) Prior Publication Data

US 2020/0261699 A1    Aug. 20, 2020

Related U.S. Application Data

(60) Provisional application No. 62/807,564, filed on Feb. 19, 2019.

(51) Int. Cl.
*A61M 25/01* (2006.01)
*A61M 25/00* (2006.01)
*A61M 25/09* (2006.01)

(52) U.S. Cl.
CPC .... *A61M 25/0158* (2013.01); *A61M 25/0067* (2013.01); *A61M 2025/015* (2013.01); *A61M 2025/0166* (2013.01); *A61M 2025/09183* (2013.01)

(58) Field of Classification Search
CPC .......... A61M 25/0158; A61M 25/0067; A61M 2025/015; A61M 2025/0166; A61M 2025/09183
See application file for complete search history.

(56) References Cited

U.S. PATENT DOCUMENTS

| | | | |
|---|---|---|---|
| 6,277,125 B1 * | 8/2001 | Barry | A61B 17/1214 606/108 |
| 8,287,584 B2 | 10/2012 | Salahieh et al. | |
| (Continued) | | | |

FOREIGN PATENT DOCUMENTS

| | | |
|---|---|---|
| WO | 2005018507 A2 | 3/2005 |
| WO | 2013088327 A1 | 6/2013 |

OTHER PUBLICATIONS

International Search Report and Written Opinion for the International Patent Application No. PCT/US2020/018575, mailed Jun. 3, 2020, 14 pages.

*Primary Examiner* — Nathan R Price
*Assistant Examiner* — John A Doubrava
(74) *Attorney, Agent, or Firm* — Seager, Tufte & Wickhem, LLP

(57) ABSTRACT

Embodiments of a deployment system may include a catheter having a distal end and a proximal end. An actuator may be disposed at the distal end of the catheter and may be operatively connected to electrical connectors extending longitudinally along the catheter from the proximal end to the actuator. The electrical connectors may be configured for transmission of signals to the actuator. One or more connections may be coupled to the actuator and to a deployable medical device disposed at the distal end of the catheter.

20 Claims, 6 Drawing Sheets

(56) References Cited

U.S. PATENT DOCUMENTS

| | | | |
|---|---|---|---|
| 2003/0028174 A1* | 2/2003 | Chan | A61M 25/0082 604/537 |
| 2005/0060030 A1* | 3/2005 | Lashinski | A61F 2/2466 623/2.37 |
| 2008/0312536 A1* | 12/2008 | Dala-Krishna | A61B 8/12 600/459 |
| 2010/0057078 A1* | 3/2010 | Arts | A61B 18/24 606/1 |
| 2013/0013057 A1 | 1/2013 | Salahieh et al. | |
| 2014/0058380 A1 | 2/2014 | Arts et al. | |
| 2014/0296962 A1* | 10/2014 | Cartledge | A61F 2/2412 623/1.11 |
| 2014/0309730 A1* | 10/2014 | Alon | A61B 17/068 623/2.11 |
| 2016/0045311 A1* | 2/2016 | McCann | A61F 2/2412 623/2.11 |
| 2018/0153689 A1* | 6/2018 | Maimon | A61F 2/2418 |
| 2019/0060057 A1* | 2/2019 | Cohen | A61F 2/2439 |

\* cited by examiner

ELECTRONIC CONTROL OF MEDICAL DEVICE DEPLOYMENT SYSTEMS AND METHODS

PRIORITY

This application claims the benefit of priority under 35 USC § 119 to U.S. Provisional Patent Application Ser. No. 62/807,564 filed Feb. 19, 2019, which is incorporated by reference herein in its entirety and for all purposes.

FIELD

The present disclosure relates generally to medical device deployment systems, and more particularly to electronic control of medical device deployment systems and methods.

BACKGROUND

Medical devices, such as implants or other interventional, endosurgical, or urological devices, may be deployable in a patient or otherwise controllable by cables mechanically actuated at a proximal end of the deployment system, e.g., external to a patient. To accommodate several cables for actuation of the medical device, the catheter may have a larger diameter along its entire length, which may result in several challenges for a medical professional. For example, a mechanical deployment system may be difficult to navigate complicated or narrow body lumens, e.g., vessels, arteries, and the like, to accurately manipulate a plurality of cables extending along an entire length of a catheter to control the medical device. A medical professional may be limited in actuation control at the proximal end of the deployment system which may result in undesirable and/or limited repeatable positioning and deployment of the medical device.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an embodiment of the present disclosure, a deployment system may include a catheter having a distal end and a proximal end. An actuator may be disposed at the distal end of the catheter and operatively connected to electrical connectors extending longitudinally along the catheter from the proximal end to the actuator. The electrical connectors may be configured for transmission of signals to the actuator. One or more connections may be coupled to the actuator and to a deployable medical device disposed at the distal end of the catheter.

In various of the foregoing and other embodiments of the present disclosure, a diameter of the proximal end of the catheter may be smaller than a diameter of the distal end of the catheter. A control box may be operatively connected to the electrical connectors at the proximal end of the catheter for sending the signals to the actuator. The deployable medical device may be positionable by the actuator in response to receiving the signals from the control box. The deployable medical device may be detachable from the one or more connections subsequent to the positioning. A support component may be extendable longitudinally along the catheter for support of the catheter. The electrical connectors may include electric wires, electronic wires, printed cables, or thermal wires, or combinations thereof. A connection to the actuators and/or the implant may be wireless. A control box may be wirelessly communicative with the actuator. A sensor may be included for detecting actuation of the one or more connections from the actuator. The control box may receive feedback to coordinate deployment of the medical device. The deployable medical device may be positionable by the actuator by linear movement, rotational movement, inch-worm actuation, rack-and-pinion actuation, a clutch mechanism, or complex displacements, or combinations thereof. The actuator may include an electric actuator, electrostatic piezoelectric actuator, thermal actuator, magnetic actuator, shape-memory material actuator, microactuator, or electroactive polymers, or combinations thereof.

According to an embodiment of the present disclosure, a method for deploying a medical device may include locating a distal end of a catheter at a desired location. The medical device may be positioned at the desired location by an actuator disposed at the distal end of the catheter. The actuator may be operatively connected to electrical connectors extending longitudinally from a proximal end of the catheter to the actuator. Signals may be transmitted by the electrical connectors to the actuator for the positioning of the medical device. One or more connections may be detached to separate the actuator and the medical device.

In various of the foregoing and other embodiments of the present disclosure, a diameter of the proximal end of the catheter may be smaller than a diameter of the distal end of the catheter. Signals may be sent to the actuator by a control box operatively connected to the electrical connectors at the proximal end of the catheter. The medical device may be positioned by the actuator in response to receiving the signals from the control box. The medical device may be detached from the one or more connections subsequent to the positioning of the medical device. The catheter may be supported by a support component extendable longitudinally along the catheter. The electrical connectors may include electric wires, electronic wires, printed cables, or thermal wires, or combinations thereof. The medical device may be positioned by the actuator by linear movement, rotational movement, inch-worm actuation, rack-and-pinion actuation, a clutch mechanism, or complex displacements, or combinations thereof. The actuator may include an electric actuator, electrostatic piezoelectric actuator, thermal actuator, magnetic actuator, or shape-memory material actuator, microactuator, or electroactive polymers, or combinations thereof. Actuation of the one or more connections from the actuator may be detected by a sensor, such that the control box receives feedback to coordinate deployment of the medical device.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1A:
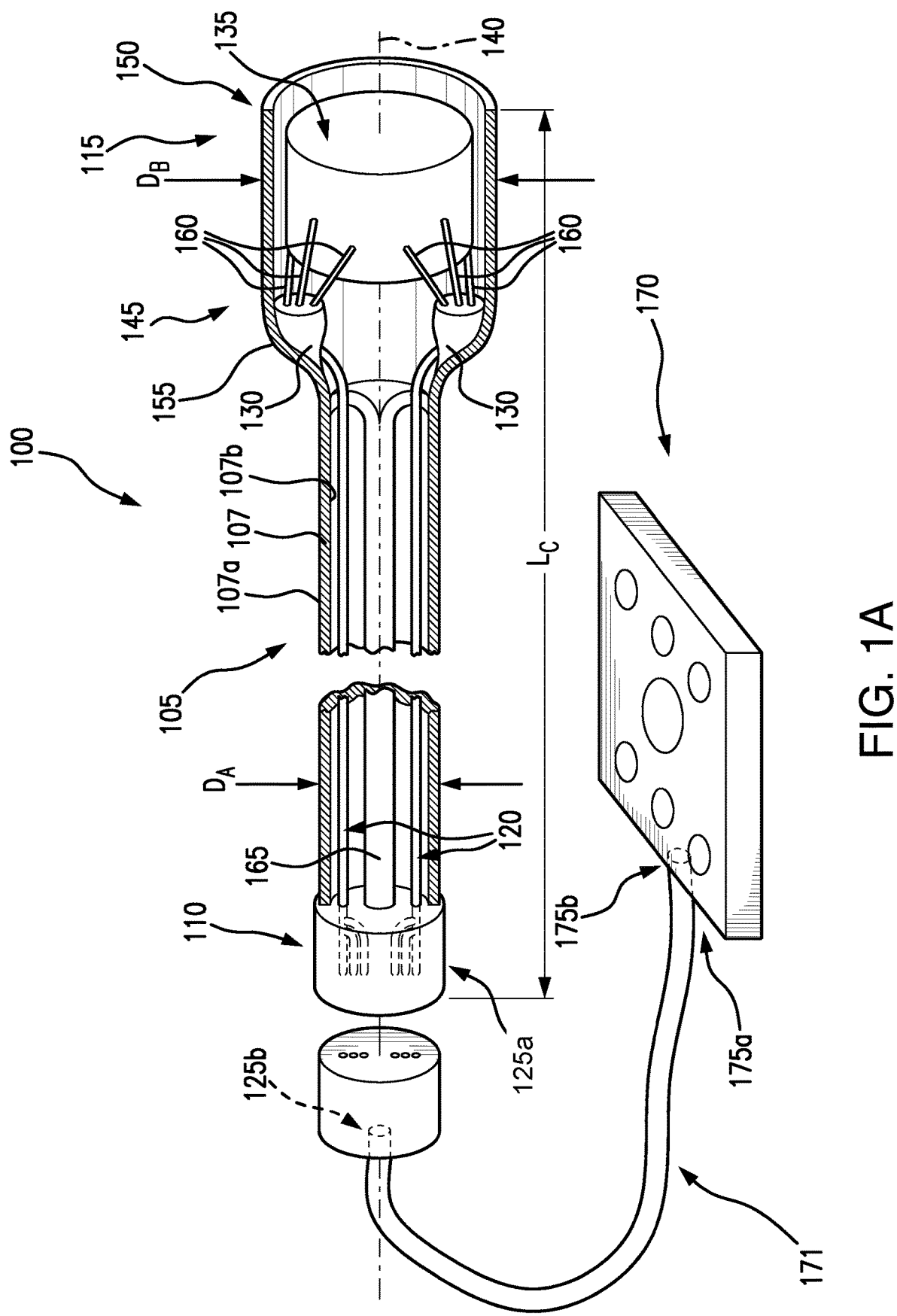
FIGS. 1A-1B illustrate embodiments of a deployment system in accordance with the present disclosure.

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements, and/or components, but do not preclude the presence or addition of one or more other features, regions, integers, steps, operations, elements, components, and/or groups thereof.

As used herein, the term "distal" refers to the end farthest away from the medical professional when introducing a medical device into a patient, while the term "proximal" refers to the end closest to the medical professional when introducing a medical device into a patient. A central axis means, with respect to an opening, a line that bisects a center point of the opening, extending longitudinally along the length of the opening when the opening comprises, for example, a tubular frame, a strut, or a bore.

Embodiments of deployment systems and methods according to the present disclosure may be configured for electronic control to improve deployment of a medical device. Electric wires and/or printed wires or cables may control high force and/or high displacement actuator(s) placed just proximal, or just distal, to the medical device for manipulation, e.g., near the intended location of the medical procedure and site for deployment in the patient. The actuator may be coupled to one or more connections for positioning the medical device in the intended location during the medical procedure, including but not limited to pushing, pulling, deploying, repositioning, and/or otherwise controlling the medical device. By reducing and/or eliminating a plurality of mechanical wires or cables necessarily extending all the way out of the patient in order for manipulation of individual elements of the medical device having multiple degrees of freedom, smaller profile catheters in accordance with the present disclosure may be included in the deployment system, which may be more flexible for medical procedures and may provide for improved overall control of the medical device. A smaller system may reduce inadvertent and/or accidental contact with tissue. Existing systems may be larger and less flexible for extending through a tortuous anatomy, e.g., aortic arch, heart chambers, at the ostia of vessels and branches, the femoral artery, and/or across the caval arch. In some patients, systems extend through organs and/or tissue anatomy that may be diseased or otherwise sensitive or damaged, such as calcified vessels, aneurysms, and/or dissections. Systems and methods of the present disclosure may reduce, minimize, and/or eliminate adverse events such as inadvertently contacting sensitive or diseased tissue which may damage tissue resulting in spasms, hemorrhage, hematomas, infections, pseudoaneurysms, cardiac tamponade, nerve injury, dissections, puncture wounds, or other types of damage.

Embodiments of the deployment systems and methods may be configured for any number of medical devices for implantation in a patient, including but not limited to cardiovascular, gastrointestinal, pulmonary, urological, and/or vascular devices, in which an electric wire or other electric connector may instead provide signals for manipulation of individual elements in multiple degrees of freedom of the medical device for deployment and positioning as desired at the intended location in the patient.

Figure 1B:
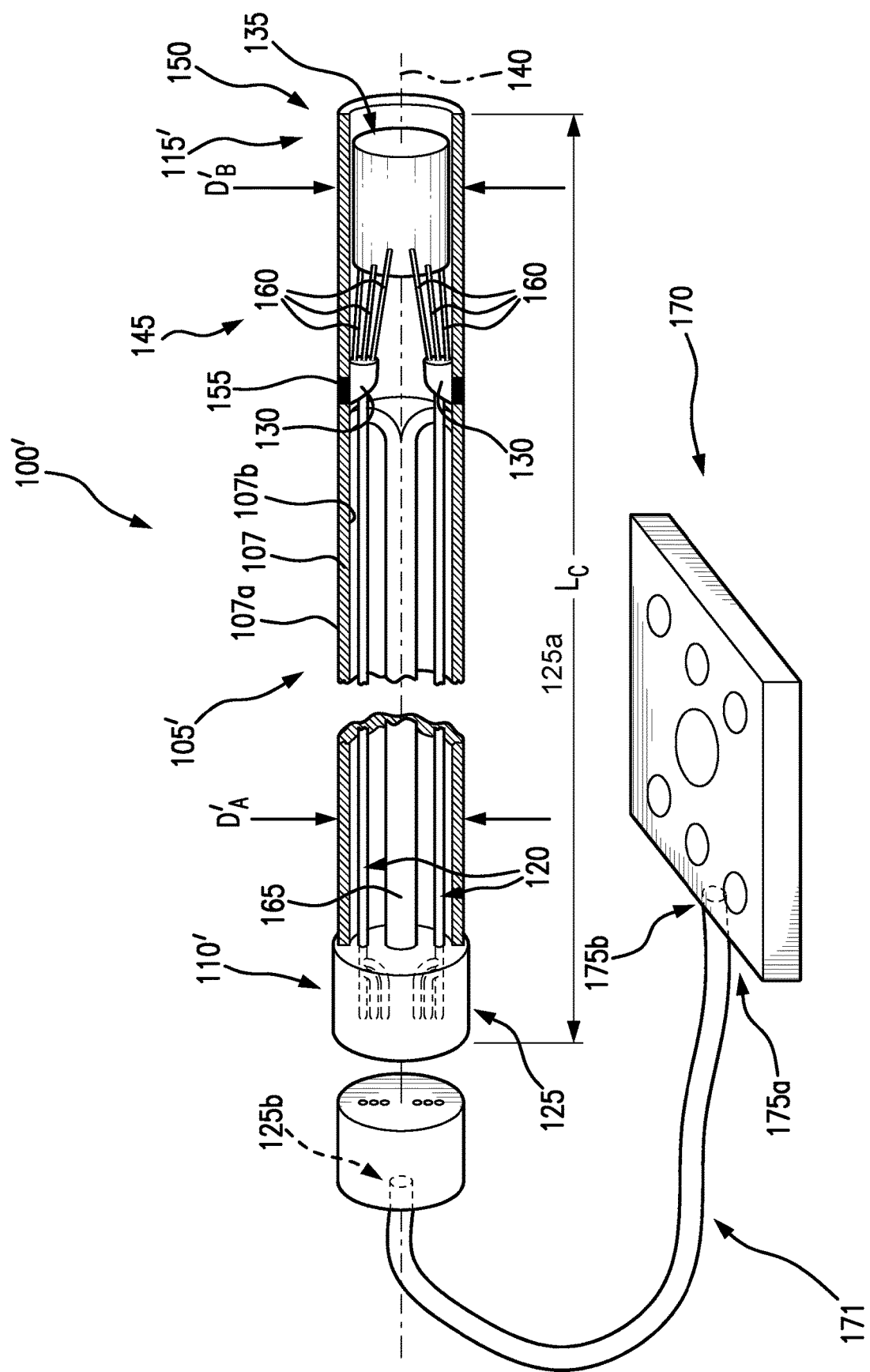

Referring now to FIGS. 1A-1B, embodiments of deployment systems 100, 100', in accordance with the present disclosure are shown. As shown in FIG. 1A, the system 100 may include a catheter 105 having a proximal end 110 and a distal end 115. The catheter 105 may be a hollow tube 107 having an outer surface 107a and an inner surface 107b, and extending along a longitudinal axis 140 a length "$L_C$". The catheter 105 may be formed of a flexible material, so that at least a portion of the length $L_C$ and the distal end 115 may navigate body lumens (which may have changing curvatures) to arrive at an intended deployment position in the patient.

In embodiments, a diameter "$D_A$" of the proximal end 110 may be smaller than a diameter "$D_B$" of the distal end 115. For example, the proximal end 110 may be sized as approximately between 2-10 Fr., and the distal end 115 may be approximately up to 30 Fr. In other embodiments, the proximal end 110 and the distal end 115 of the catheter 105 may be substantially the same, e.g., $D_A$ may be approximately equal to $D_B$. As shown in FIG. 1B, for example, another embodiment of a deployment system 100' may include a catheter 105' having a proximal end 110' and a distal end 115', in which a diameter "$D'_A$" of the proximal end 110' may be equal to a diameter "$D'_B$" of the distal end 115'. Additional components described herein may be included in deployment systems 100, 100'.

The distal end 115, 115' of the catheter 105, 105' may have a proximal portion 145 and a distal portion 150. As shown in FIG. 1A, the distal end 115 may gradually transition from the diameter $D_A$ at the proximal portion 145 to the diameter $D_B$ at the distal portion 150 and/or may extend in stepped portions, such that the distal end 115 may form a frusto-conical shape. In other embodiments, the proximal portion 145 and the distal portion 150 may have substantially the same diameter, e.g., as shown in FIG. 1B.

The proximal portion 145 of distal end of the catheter may include a reinforced area 155 for supporting an actuator 130. The reinforced area 155 may be a substantially inflexible portion of the catheter 105, 105' to minimize collapse, kinking, and/or constriction at the reinforced area 155 as the catheter 105, 105' is navigated in the patient. In some embodiments, the reinforced area 155 may be a strengthened portion of the hollow tube 107. The reinforced area 155 may be formed of a different material and/or include additional elements as compared to other portions of the catheter 105, 105' to have a higher strength at the reinforced area 155. In some embodiments, the reinforced area 155 may include additional attachments of the actuator 130 to the hollow tube 107. The reinforced area 155 may be included so that the catheter may withstand 'reaction' forces and/or torques applied during deployment of a selected medical device. In some embodiments, a reinforced area 155 may align with the diameter transition from the diameter $D_A$ of the proximal end 110 to the diameter $D_B$ of the distal end 115, as shown in FIG. 1A.

The catheter 105, 105' may have a uniform wall thickness of the hollow tube 107 throughout the length $L_C$ of the catheter 105, 105' although in some embodiments, a wall thickness may taper from a thicker wall thickness at the proximal end 110, 110' of the catheter 105, 105' to a thinner wall thickness at the distal end 115, 115' of the catheter 105, 105'. A wall thickness of the catheter 105, 105' may be uniformly thinner along the length $L_C$ of the catheter 105, 105' as compared to existing delivery systems by removal of bulkier mechanical cables.

The proximal end 110, 110' may remain external to a patient during a medical procedure, to allow a medical professional to control the distal end 115, 115' at the intended internal position for the procedure. The catheter 105, 105' may be insertable in a patient, with the distal end 115, 115' being positionable at a desired location for deploying a medical device. For example, an implant may be deployed for repairing a heart valve, an occlusion device may be positioned for redirecting and/or preventing fluid flow in a body lumen, or any other number of grafts, stents, or other medical devices may be temporarily or permanently inserted in a patient by the system 100, 100' to improve patient health. In some embodiments, the systems 100, 100' may be used for actuating an accessory, such as biopsy forceps, graspers, snares, needles, or other instruments used in various applications such as endoscopic and/or pulmonary applications.

The system 100, 100' may include electrical connectors 120, extending the length of the catheter 105, 105', e.g., from the proximal end 110, 110', to the distal end 115, 115'. The electrical connectors 120 may be operatively connected to a control box 170 disposed at the proximal end 110, 110'. The control box 170 may be configured to provide signals to an actuator 130 at the distal end 115, 115' of the system 100, 100' by the electrical connectors 120.

Electrical signals controlling the deployment of the medical device 135 may allow for improved repeatability and precision for placement at the intended location in the patient by providing a more controlled positioning and deployment of the medical device through the actuator 130 at the distal end 115, 115' of the catheter 105, 105'. This control of a procedure may in some embodiments reduce procedure times and/or may allow for better and/or safer tracking of the system 100, 100' to the intended delivery location of the patient.

The electrical connectors 120 may be operatively connected to the actuator 130 for receiving electrical signals to actuate and deploy a medical device 135 to a desired position in the patient. In some embodiments, the control box 170 may be connected to the electrical connectors 120 via a cable 171 and may be connectable by connectivity components 125b and 175b as plug-in snap connections to respective connectivity component 125a at the proximal end 110, 110' of the catheter and 175a at the control box 170. In some embodiments, the control box 170 may be wirelessly connected to the electrical connectors 120. In some embodiments, the control box 170 may be wirelessly connected to the actuators 130 for communicating operation, release, or otherwise manipulation of the device 135, e.g., Bluetooth, radio-frequency identification, or the like). In some embodiments, the control box 170 may be individually designed to the medical device for deployment, and in other embodiments the control box 170 may be an off-the-shelf design configured to deploy a plurality of different medical devices.

The electrical connectors 120 may extend longitudinally along the length $L_C$ and substantially parallel to the longitudinal axis 140 of the catheter 105, 105', from the connectivity component 125a for connection with the control box 170 at the proximal end 110, 110' to the actuator 130 at the distal end 115, 115'. The electrical connectors 120 may be disposed along the outer surface 107a of the catheter 105, 105', along the inner surface 107b of the catheter 105, 105', in the hollow tube 107 of the catheter 105, 105', and/or embedded in the hollow tube 107 of the catheter 105, 105'. In some embodiments, the electrical connectors 120 may be within the wall of the hollow tube 107. The electrical connectors may be one or more wires, including but not limited to electric wires, electronic wires, printed cables, or thermal wires, or combinations thereof. The electrical connectors 120 may include insulated wires, fine gage wires, and/or printed electronics for transmitting voltages and currents to the actuator 130. To account for potential tortuous anatomies as the system 100, 100' is delivered to the intended location of the medical procedure, the electrical connectors 120 may be formed straight and/or serpentine to build in slack in the connector to allow for bending of the catheter 105, 105' to minimize a risk of damaging and/or breaking the electrical connectors 120 under larger displacements, strains, and/or stresses. In some embodiments, the electrical connectors may be attached to the catheter outer surface 107a and/or inner surface 107b by flexible glues and/or other adhesives that allow for a flexibility to accommodate changing curvatures of the catheter 105, 105' during delivery to the intended location of the medical procedure. The electrical connectors 120 may additionally and/or alternatively include an insulation and/or coating to protect the electrical integrity during normal use and/or sterilization of the system 100, 100', which may not alter the flexibility of the electrical connectors 120 and/or attachment to the catheter 105, 105'.

The electrical connectors 120 may replace larger mechanical cables for individual element manipulation in existing systems, so that the diameter $D_A$ of the proximal end 110 of the catheter 105 may be smaller in size, thereby improving access to and delivery through the patient, as shown in FIG. 1A. In some embodiments, the catheter 105' may have a constant diameter thickness, so that the proximal end diameter $D'_A$ is approximately equal to the distal end diameter $D'_B$, as shown in FIG. 1B.

The diameter $D_A$ of the proximal end 110 may extend substantially the length $L_C$. When the catheter 105 has a variable diameter, this reduced proximal and mid-catheter diameter may limit a "pushability" of the catheter 105, such that the catheter 105 may be subject to kinking, or collapse, or both. Kinking and/or collapse may be a function of the larger diameter $D_B$ of the distal end 115 to accommodate a larger medical device 135. It is also understood that a catheter 105' having a constant diameter at the proximal and distal ends 110', 115', may also be subject to kinking and/or collapse.

A support component 165 may be included in the systems 100, 100', and may be disposed in the catheter 105, 105' and extending along the catheter 105, 105' to the distal end 115, 115'. A support component 165 may be included to strengthen and/or support the catheter 105, 105' along its length $L_C$, and may be formed as a straight rod, and/or a spiral rod. The support component 165 may be formed as a wire and may be any material having sufficient strength for applying forces to the proximal portion 145 of the distal end 115, 115' of the catheter 105, 105', or to the reinforced area 155, including but not limited to composites. In embodiments, the support component 165 may be formed having a uniform diameter, although in some embodiments, the support component 165 may be a variable diameter to enhance flexibility.

The support component 165 may extend substantially parallel along the longitudinal axis 140 of the length $L_C$ of the catheter 105, 105'. The support component 165 may be disposed substantially along a center of the hollow tube 107, and/or extend along the inner surface 107b. In some embodiments, a support component 165 formed as a spiral may extend along the inner surface 107b of the catheter 105, 105', which may be advantageous to enhance flexibility and/or torque forces applied to the actuator 130. In some embodiments, the support component 165 may be a single rod, and/or may include a plurality of support components.

The actuator 130 may be disposed in the proximal portion 145 of the distal end 115, 115' of the catheter and may include a single actuator, or any number "n" actuators 130a, 130b, . . . 130n, for deploying the medical device 135. In some embodiments, the actuator 130 may be disposed in the distal portion 150 of the distal end 115, 115'. The actuator 130 may be configured to provide sufficient forces needed for deployment of the selected medical device 135, and may be individualized depending on the selected medical device 135. For example, different forces, e.g., linear, rotational, varying distances, etc., may be necessary for deploying the medical device depending on the anatomy of the intended location of the medical procedure. The actuator 130 may be an electric actuator, electrostatic piezoelectric actuator, thermal actuator, magnetic actuator, shape-memory material actuator, microactuator, or electroactive polymers, or combinations thereof, to deploy the medical device 135 at the intended location of the procedure. The actuator 130 may be configured for various movement to position the medical device 135, including but not limited to linear movement, rotational movement, inch-worm actuation, rack-and-pinion actuation, a clutch mechanism, or complex displacements, or combinations thereof. The actuator 130 may be configured for supporting a wide range of operational parameters including but not limited to electrical currents, forces, torques, and/or dimensions, although in some embodiments an actuator 130 having a narrower range of operational parameters may be used depending on the selected medical device and intended location for the medical procedure.

In some embodiments, operational parameters of the actuator 130 may not be sufficient for deploying the selected medical device 135 at the intended location of the medical procedure. The actuator 130 may then utilize a lower energy and/or displacement force to release a latch or other element to release a mechanism such as a linear spring, rotational spring, chemical reaction, or other energy source, that may generate sufficient forces to deploy the selected medical device 135. For example, a spring may be held in a compressed position having a stored energy. The actuator 130 may initiate movement to release the spring, allowing the spring to expand and thus apply forces to the selected medical device 135. The applied forces may be sufficient to deploy the selected medical device 135 from the distal end 115, 115' of the catheter 105, 105' as desired by the medical professional. In some embodiments, the systems 100, 100' may include mechanical actuating cables or wires in addition to the electrical connectors 120 and actuators 130. This may be advantageous to overcome potential limitations in the forces, torque, displacement, rotations, energy, and the like applicable by the actuators 130.

The actuator 130 may be configured to deploy, e.g., push, at least a portion of the medical device 135 out of the distal end 115, 115' of the catheter 105, 105'. In some embodiments where the medical device 135 is formed of a shape memory material such as nitinol, the actuator 130 may be configured to unsheath, unconstrain, or otherwise release, at least a portion of the medical device 135 for expansion in the intended location of the procedure. In some embodiments, the actuator 130 may be configured to move and/or rotate at least a portion of the medical device 135. In some embodiments, the actuator 130 may be configured to reposition at least a portion of the medical device 135. In some embodiments, the actuator 130 may be configured to release therapeutic drugs or other agents from a reservoir or other compartment of the medical device 135 and/or the catheter 105, 105' (not shown). In some embodiments, therapeutic drugs or other agents may be pre-loaded in the catheter 105, 105' and/or medical device 135.

The actuator 130 may be configured to deploy the medical device 135 by connections 160. The one or more connections 160 may be removably coupled to the actuator 130 and to the medical device 135. The one or more connections 160 may be sutures, strings, cables, sheaths, shape-memory material, screws, or any other material or geometry to retain the medical device 135 in the distal end 115, 115' of the catheter 105, 105' until deployment at the intended location of the medical procedure. The one or more connections 160 may include a release element, such as hooks, knots, adhesives, electromechanical, electrochemical detachment mechanisms, or other joining mechanisms, so that a medical device may be detachable from the one or more connections subsequent to deployment and satisfactory positioning at the intended location of the medical procedure.

The one or more connections 160 may be coupled to the actuator 130 and/or medical device 135 using multiple configurations such as screws and bolts, pins, hooks, weld joints, adhesives, magnets, and/or interference fits (where force and/or an actuated shape memory expansion or contraction may initiate release), and the like, or various combinations thereof. These couplings may be designed for the individual actuator 130 and/or medical device 135, and may be manufactured using microfabrication processing based on the size, force, torque, thermal, magnetic, and/or additional design requirements. In other embodiments, the couplings may be off-the-shelf designs configured for accommodating a variety of different medical devices.

Figure 4A:
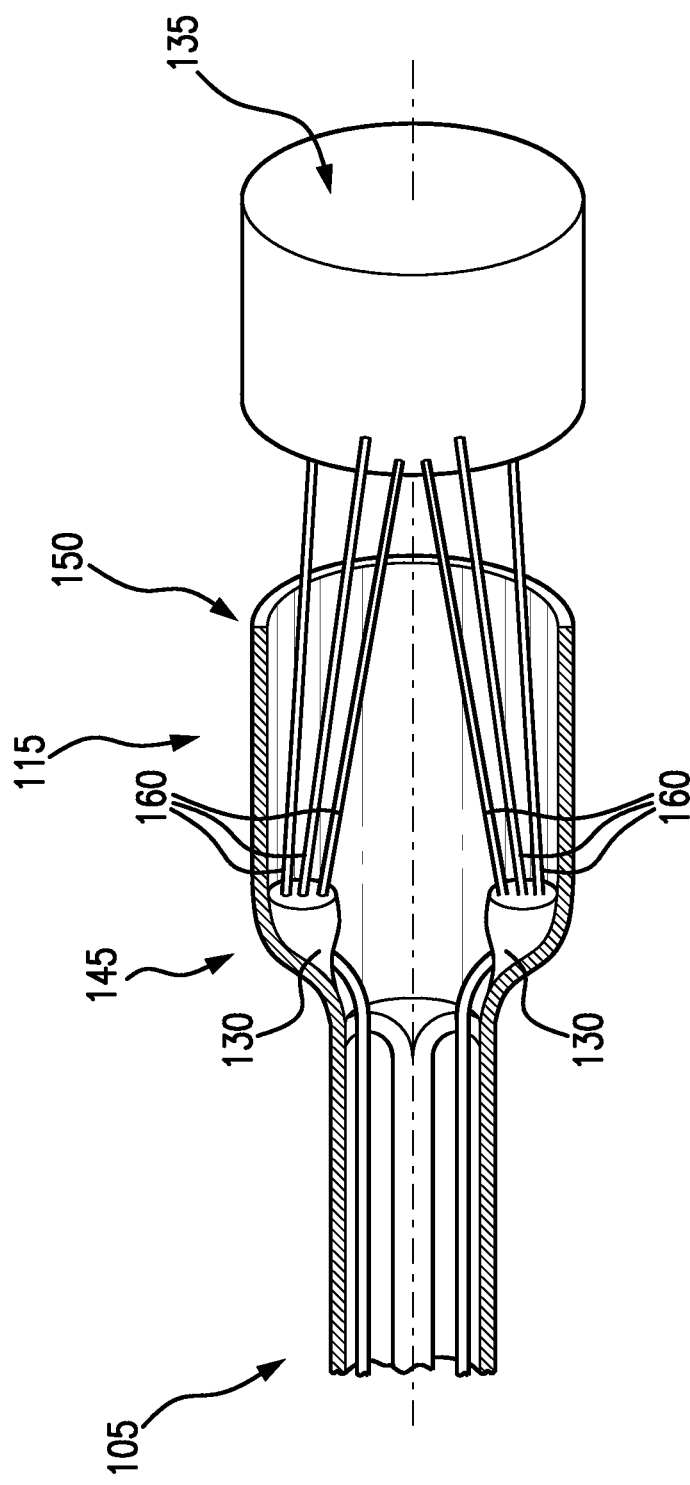
FIGS. 4A-4B illustrate an method for deploying a medical device in accordance with the present disclosure.
Figure 4B:
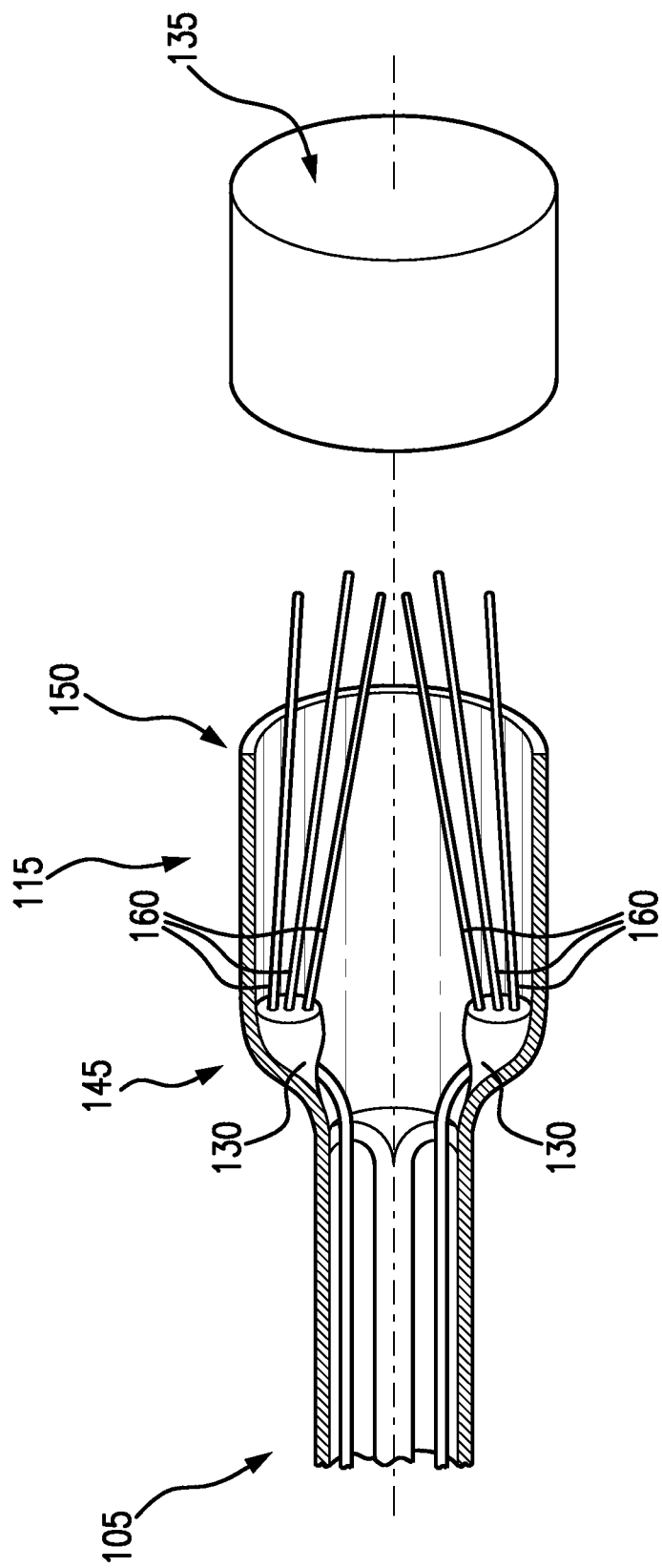

In some embodiments, the connections 160 may be of a predetermined length, so that the medical device 135 is extendable out of the distal end 115, 115' of the catheter 105, 105' via the actuator 130 to a predetermined distance (see e.g., FIG. 4B). In some embodiments, the connections 160 may be formed of a shape memory material, so that the connections 160 are in a compressed state while the medical device 135 is in the distal end 115, 115' of the catheter 105, 105'. Upon deployment of the medical device 135 by the actuator 130, the connections 160 may be uncompressed to allow positioning of the medical device a distance out of the distal end 115, 115' of the catheter 105, 105'.

Figure 2A:
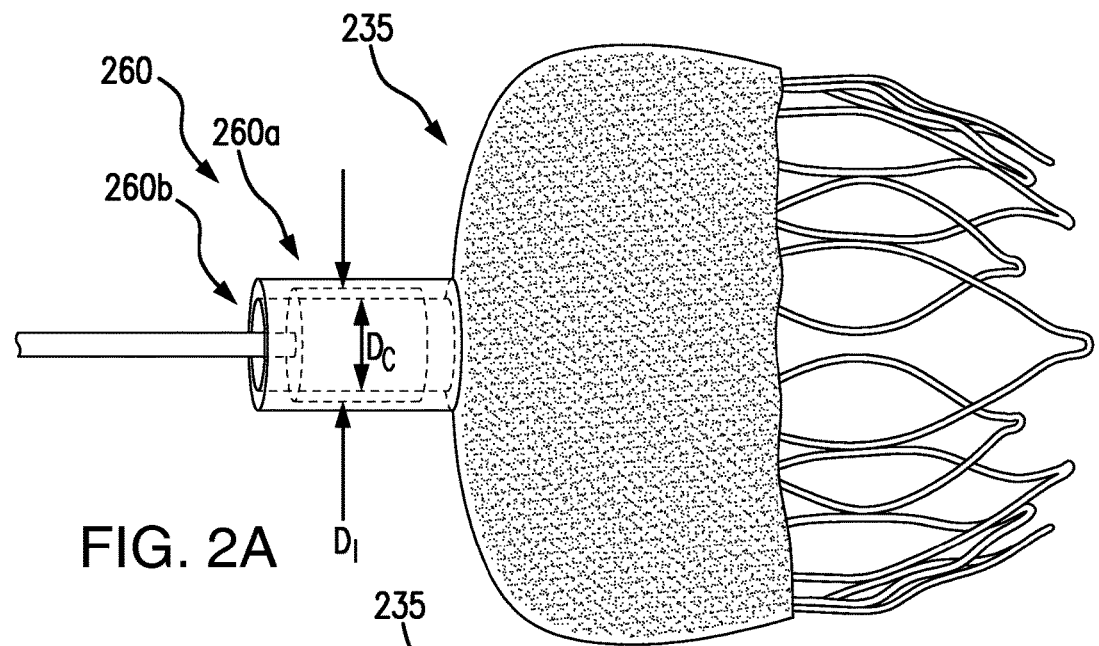
FIGS. 2A-2C illustrate embodiments of connection mechanisms between a medical device and a catheter of a deployment system in accordance with the present disclosure.
Figure 2B:
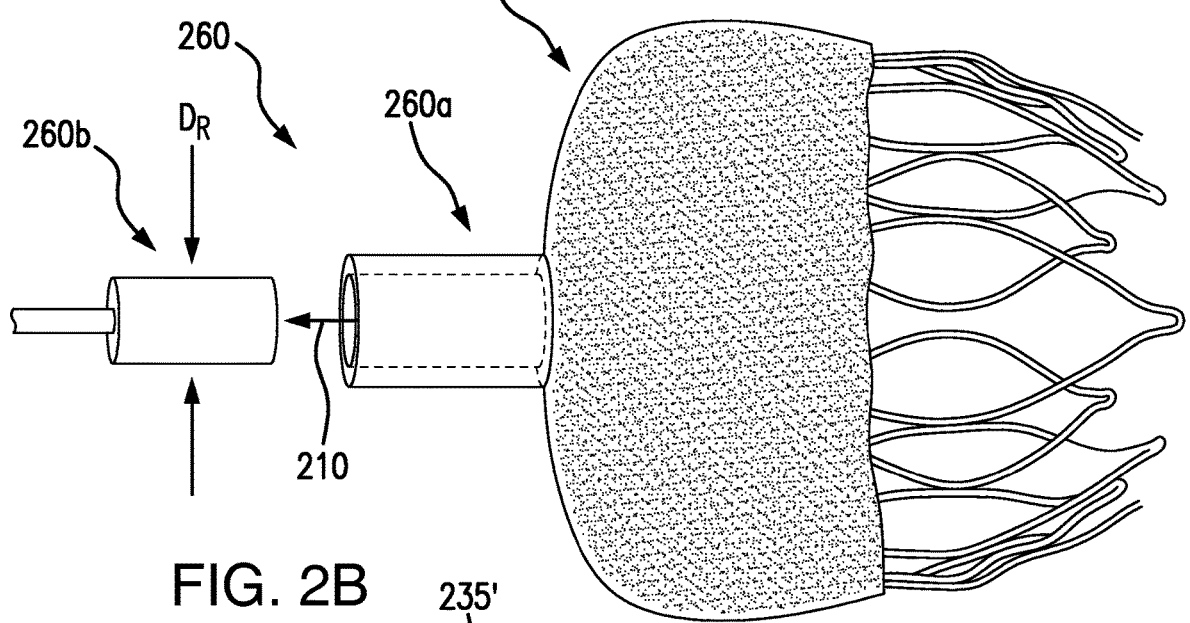
Figure 2C:
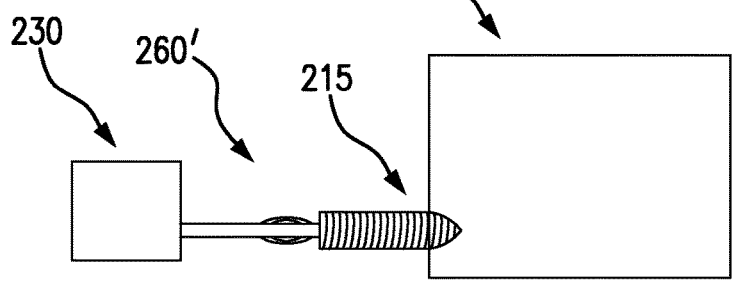

In some embodiments, as shown in FIGS. 2A-2C, a connection mechanism between a medical device and a catheter may be included in a deployment system. A deployable medical device, or implant, 235, 235' may include a connection 260 between the medical device 235, 235' and the deployment system, e.g., an actuator and/or catheter. The connection 260 may include a first component such as a medical device connector 260a, and a second component such as a deployment system connector 260b. The first component 260a may be a tube, or cap, or any other shape configured to receive and/or mate with the second component 260b.

In some embodiments, the second component 260b may be coupled to an actuator, although in other embodiments, the second component 260b may be coupled to an inner portion of a catheter for deploying the medical device 235, 235'. The first and second components 260a, 260b may be initially coupled, as shown in FIG. 2A, so that the separation may occur only when the medical device 235, 235' is placed in position as desired.

In embodiments, the second component 260b may have an initial diameter "$D_I$," which may be slightly larger than inner diameter "$D_C$" of the first component 260a, so that the first and second components 260a, 260b are fixedly coupled by an interference fit. As shown in FIG. 2B, when the medical device 235, 235' is deployed to a desired location, the second component 260b diameter may be reduced to "$D_R$," which may be less than the initial diameter $D_I$, as well as the inner diameter $D_C$ of the first component 260a. When the second component 260b is at the reduced diameter $D_R$, the first and second components 260a, 260b may be separated from each other, e.g., by retracting in a proximal direction indicated by arrow 210. This may separate, or decouple, the medical device 235, 235' from the catheter, as shown in FIG. 2B. Although the first and second components 260a, 260b of the connection 260 are shown in FIGS. 2A-2B as cylindrical components, it is understood that the connections may be any shape configured to be detachably connectable to each other.

The second component 260b may be configured, such that the diameter may be adjustable by known means. The second component 260b may be formed of a compliant material. In some embodiments, the diameter may be adjusted by a mechanism operable via an actuator. For example, the second component 260b may be wound, or twisted, e.g., by a motor, to reduce the diameter from the initial diameter $D_I$ to the reduced diameter $D_R$. As the second component 260b is wound, the compliant material may compress, thereby reducing the diameter enough to decouple from the first component 260a. In some embodiments, the second component 260b may be deflatable, e.g., a fluid may be utilized to adjust the diameter between the initial diameter $D_I$ and the reduced diameter $D_R$. For example, a fluid may be flowed in and/or out of the second component 260b for inflation and/or deflation, thereby adjusting the diameter as desired. In some embodiments, the second component 260b may include a mechanism for expanding and/or contracting the second component 260b. For example, a plurality of arms may be connected to an actuator which may be movable between an expanded, or coupled position, and a retracted, or decoupled, position.

Additionally and/or alternatively, as shown in FIG. 2C, a medical device 235' may include one or more connections coupled between an actuator 230 and the medical device 235'. In some embodiments, the medical device 235' may be medical device 135, 235. A connection 260' may be detachably coupled to the medical device 235' by a screw 215. The actuator 230 may include a micro-motor for rotation of the screw 215 and/or connection 260'. The screw 215 may be connected to a portion of the medical device 235', and in some embodiments may include a plurality of screws 215 coupled to a plurality of connections 260'. In some embodiments, the screw 215 may be configured to attach to a patient, thereby securing the medical device 235' in the patient. In some embodiments, the screw 215 may be any connection mechanism, including but not limited to a screw, clip, helical anchor, and/or hook. The screw 215 may be adjustable by the connection 260' to push, pull, and/or rotate the medical device 235' for positioning in the patient prior to decoupling.

Understanding the forces applied to the medical device 135, 235, 235' may be difficult for a medical professional to determine by visualization only. Additionally, some procedures may be difficult to visualize, such that placement of the device may be compromised. Sensors or microsensors, e.g., force, torque, linear displacement, rotational displacement, temperature, PH, flow, accelerometers, pressure, 3-D compasses, gyroscopes, and the like, may be included in the system 100, 100' to improve the deployment of the medical device 135, 235, 235', by allowing the medical professional to receive feedback via the sensors, electrical connectors, and/or control box, and from the system 100, 100' and make adjustments accordingly. For example, sensor feedback may coordinate single or multiple actuations, e.g., for adjusting the medical device mid-deployment, and/or adjusting the application of force on the device. The system 100, 100' may receive sensor feedback allowing for the medical professional to manually adjust operational parameters, although the system 100, 100' may also be configured for the control box 170 to receive sensor feedback for verification of the deployment and allow the next signals to be sent. If the sensor feedback indicates that the medical device is incorrectly positioned, an alert may indicate to the medical professional that manual adjustment may be needed, and/or if the procedure may continue or be aborted.

Sensor feedback may be advantageous for a medical professional for procedures where visualization is difficult, e.g., procedures performed under fluoroscopy or other image guidance to the intended location of the procedure. As described below with respect to FIGS. 3A-3B, for example, sensors may detect a deployment distance and/or number of rotations of anchors to secure a medical device 335 to tissue.

Figure 3B:
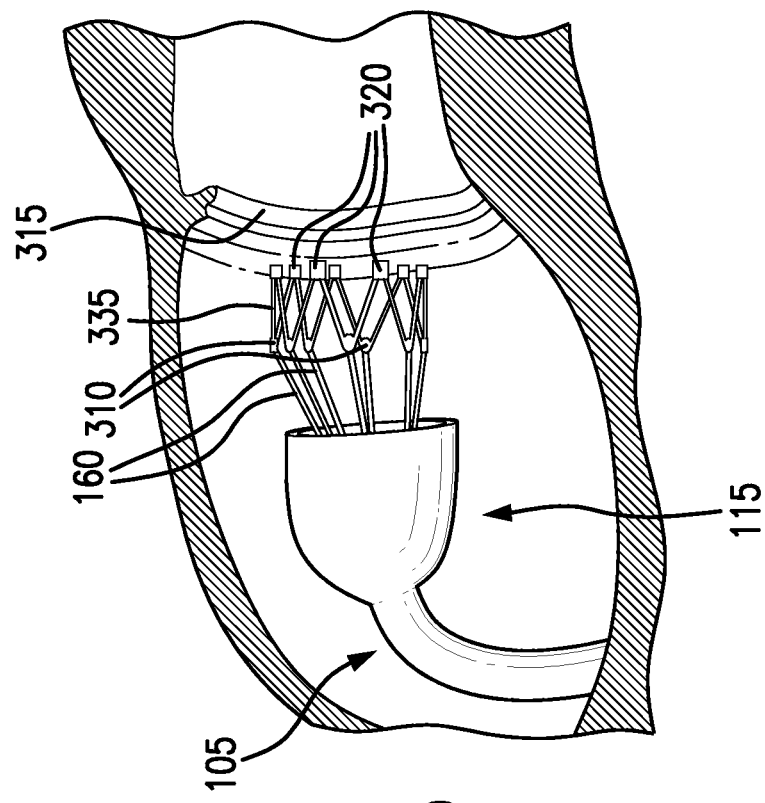
FIGS. 3A-3B illustrates an embodiment of an implant deployment system in accordance with the present disclosure.
Figure 3A:
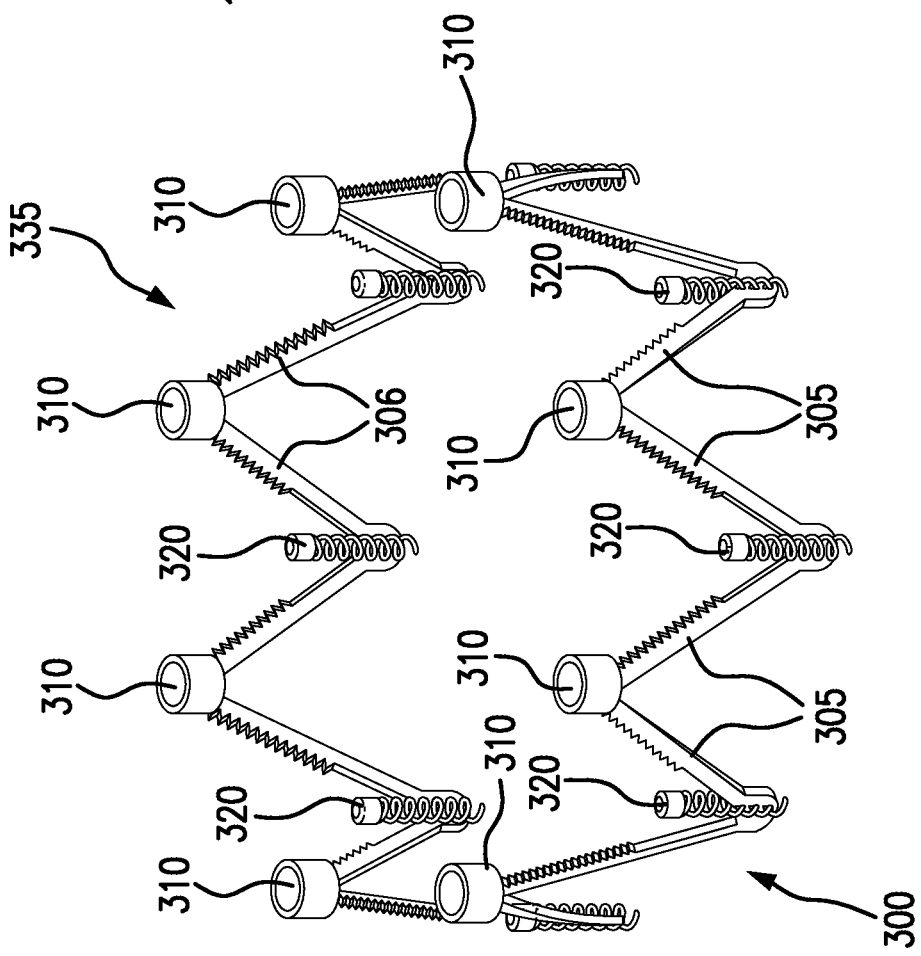

Referring now to FIGS. 3A-3B, an embodiment of a medical device is illustrated, e.g., as medical device 335. As described above, a medical device may be any number of medical devices for deployment in a patient, including but not limited to temporary and/or permanent implants, and may be deployable in various body lumens and/or organs of the patient including for example, cardiovascular, gastrointestinal, urological, and/or other vasculature.

In some embodiments, each connection 160 may be removably attached to an element of the medical device 335 for manipulation. For example, in some embodiments, the medical device 335 may include a plurality of elements having multiple degrees of freedom. Each connection 160 may manipulate each element to move the medical device 335 as desired. The connections 160 may be individually controllable and operable by the actuator or multiple actuators 130, which may receive signals for each connection, to manipulate each element in a selected order to deploy and position the medical device 335 as desired.

The medical device 335 illustrated may be deployable in a patient's heart valve, e.g., as a transcatheter annuloplasty ring 300. The ring 300 may include a plurality of struts or arms 305 connected to form the ring 300, and movably coupled (e.g., hingedly coupled) to each other such as by connector 310. In some embodiments, the connector 310 may be an actuatable sliding coupler. Each arm 305 may be hingedly coupled to the adjacent arm 305 at the connector 310, such that the ring 300 may be movable from a first, compressed position, to a second, expanded position, as shown in FIG. 3A. A connection 160 may be connected at each connector 310 and attached to the actuator 130 to move the ring 300 from the first compressed position to the second expanded position.

The ring 300 may be in the first compressed position at the distal end 115 of the catheter 105 before deployment. It is also understood that catheter 105', in which a proximal end 110' has a diameter substantially equal to the distal end 115', may be used to deploy the ring 300. The connections 160 may be compacted, or compressed, between the actuator 130 and the ring 300 prior to deployment. When the distal end 115, 115' of the catheter 105, 105' is positioned at the intended location for the procedure, one or more signals may be sent from the control box 170 to the actuator 130 via the electrical connectors 120. When the actuator 130 receives the signals, the actuator may actuate each connection 160 as per the signal for deployment (e.g., as shown in FIGS. 1A-1B). In some embodiments, the connections 160 may be extended a predetermined linear distance, e.g., substantially parallel to the longitudinal axis 140, without expanding the ring to the second expanded position, so the ring 300 is extended out of the distal end 115, 115' of the catheter 105, 105' but still in a first, compressed position. For example, the arms 305 may be held in a substantially closed position by the connector 310, and the actuator 130 may not actuate the connection 160 to manipulate the connector 310 to expand the arms 305.

When the connections have been extended to the predetermined linear distance, the actuator 130 may receive additional and/or alternative signals from the control box 170 to actuate the ring 300 in a radial direction. For example, the ring 300 may be moved to the second expanded position by the actuator 130 actuating the connections 160 to manipulate the connector 310, such that the adjacent arms 305 are pivoted or rotated outward to move the ring 300 to the second expanded position.

Signals may continue to be sent to the actuators in a desired order to expand and/or position the ring 300 at the right or left atrium for repair of the tricuspid or mitral valve. The signals may be pre-programmed for deploying the ring 300, signals may be sent based on sensor feedback of the positioning of the ring, and/or a medical professional may manually input instructions for sending signals to position based on visualization and/or other feedback. The ring 300 may be positioned in proximity to the valve 315 for attachment, e.g., via helical anchors 320, and signals may be sent to the actuator 130 to adjust the connections 160 individually and/or as a group to align with the valve 315. Upon alignment, the anchors 320 may be attached to annulus tissue surrounding the valve 315, while the connections 160 are still attached to the connectors 310. When the ring 300 is attached to the annulus tissue, signals may be sent from the control box 170 to the actuator 130 to manipulate the connections 160 to move the ring 300 from the second expanded position, to a third, repaired position. For example, the mitral or tricuspid valve 315 may be wider due to disease such that the valve may not fully close during pulsation of the heart. The ring 300 may be contracted to draw in the surrounding annulus tissue to valve 315, thereby providing full closure. The connections 160 may be actuated by signals from the control box to position the ring 300 as desired, e.g., by hingedly opening and/or closing the arms 305, to close the valve 315. When the ring 300 has been positioned as desired, the anchors 320 may be fully implanted to secure the annulus tissue. The connections 160 may be disconnected from the connectors 310 to separate the ring 300 from the catheter 105, 105' and the catheter may be retracted from the patient.

Referring now to FIGS. 4A-4B, an embodiment of a process of deploying a medical device from a catheter is illustrated. A medical device 135 may be retained in the distal end 115, 115' of the catheter 105, 105' by one or more connections 160, and it is understood that the process described may be applied to any of the medical devices 135, 235, 235', 335 described herein. To perform a medical procedure, the distal end 115, 115' of the catheter 105, 105' may be inserted into a patient at an access point, which may vary depending on the procedure and the device for deployment. The medical professional may continue extending the catheter 105, 105' into the patient until coming within proximity to the intended location of the procedure. The medical professional may adjust the distal end 115, 115' of the catheter 105, 105' so that the distal portion 150 is facing the desired deployment position of the medical device. The proximal end 110, 110' of the catheter, and the control box 170 may remain external to the patient, e.g., outside of the access point.

When the distal portion 150 of the distal end 115, 115' is in position, signals may be sent from the control box 170 via the electrical connectors 120 to the actuator 130 at the proximal portion 145 of the distal end 115, 115' of the catheter 105, 105'. The signals may initiate action by the actuators 130, such that connections 160 coupled to the actuator 130 and the medical device 135 may extend the medical device 135 distally out of the distal end 115, 115' of the catheter, as shown in FIG. 4A. In some embodiments, a cable, or wire actuation system, may retract the distal end 115, 115' of the catheter 105, 105', thereby at least partially enabling deployment of the medical device 135. Actuators 130 and/or the connections 160 may initiate the operation for completing deployment of the medical device 135. The signals may control the actuator 130 such that the connections extend the medical device 135 linearly, radially, rotationally, or any other type of movement, or combinations thereof. In some embodiments, the actuator 130 may first extend the medical device 135 only in a linear direction to exit the catheter 105, 105', and then proceed to more complex movements by the connections 160 once the medical device is free of the catheter 105, 105'.

As shown in FIG. 4B, after the medical device 135 has been extended out of the catheter 105, 105'; the connections 160 may expand the medical device 135, e.g., larger than the diameter $D_B$ of the distal end of the catheter. Medical devices may be in a compressed state to allow for travel through the patient to the intended location of the procedure, requiring subsequent expansion or allowing for self-expansion, prior to placement and/or attachment to surrounding tissue. The actuator may receive signals from the control box 170 to perform this expansion after extending the device 135 out of the catheter 105, 105' or the device 135 may be self-expanding.

The medical professional may verify placement of the device 135, and additional signals may be sent to the actuator 130 for fine tune adjustment for final positioning in the patient. Depending on the type of medical device 135, it may be attached to surrounding tissue prior to separation of the connections 160 by additional actuation, although in some embodiments, the medical device 135 may self-position and/or align, and/or not require attachment to tissue.

When the medical device 135 is in position, the connections 160 may be separated from the device 135. The connections 160 may have mechanisms for separation, such as hooks, screws, adhesives, clips, or other attachments, including as described above. After separation, the catheter 105, 105' may be removed from the patient.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A deployment system, comprising:
   a catheter having a distal end and a proximal end and defining a lumen therethrough;
   an electrically controlled actuator mounted and supported on an area on the interior of the lumen in the distal end of the catheter; and
   one or more connections extending distally from the actuator and positioned and coupled between the actuator and a deployable medical device disposed within the lumen of the catheter at the distal end of the catheter;
   wherein:
   the actuator is selectively movable to move the one or more connections individually or as a group to adjust the position of the medical device after the medical device has been attached to tissue and while the medical device is coupled with the one or more connections; and
   the one or more connections are separable from the medical device after the medical device has been deployed and secured to a patient.

2. The system according to claim 1, wherein a diameter of the proximal end of the catheter is smaller than a diameter of the distal end of the catheter.

3. The system according to claim 1, further comprising electrical connectors extending longitudinally along the catheter from the proximal end to the electrically controlled actuator, the electrical connectors configured for transmission of signals to the electrically controlled actuator, and further comprising a control box operatively connected to the electrical connectors at the proximal end of the catheter for sending the signals to the electrically controlled actuator.

4. The system according to claim 1, further comprising a sensor to provide feedback for adjusting control of the actuator to coordinate deployment of the medical device to adjust the medical device mid-deployment.

5. The system according to claim 1, wherein the deployable medical device is positionable by the electrically controlled actuator by linear movement, rotational movement, inch-worm actuation, rack-and-pinion actuation, a clutch mechanism, or complex displacements, or combinations thereof.

6. The system according to claim 1, further comprising a support extendable longitudinally along the catheter and configured to support the catheter.

7. The system according to claim 1, further comprising a control box wirelessly communicative with the electrically controlled actuator.

8. The system according to claim 1, wherein the electrically controlled actuator includes an electric actuator, electrostatic piezoelectric actuator, thermal actuator, magnetic actuator, shape-memory material actuator, microactuator, or electroactive polymers, or combinations thereof.

9. The system according to claim 1, wherein the electrically-controlled actuator is configured to deploy the deployable medical device, and the one or more connections are removably coupled to the electrically-controlled actuator.

10. The system according to claim 1, wherein the one or more connections comprise a plurality of connections, each connection controlling a different element of the medical device while the medical device is attached to tissue to adjust the configuration of the medical device and the tissue.

11. The system according to claim 3, wherein the deployable medical device is positionable by the electrically controlled actuator in response to receiving the signals from the control box.

12. The system according to claim 3, wherein the electrical connectors include electric wires, electronic wires, printed cables, or thermal wires, or combinations thereof.

13. A method for deploying a medical device, comprising:
   locating a distal end of a catheter with a medical device disposed within a lumen thereof at a desired location;
   extending the medical device out of the lumen of the catheter and positioning the medical device at the desired location by an electrically controlled actuator mounted and supported on an area on the interior of the lumen in the distal end of the catheter and coupled with the medical device with one or more connections, the electrically controlled actuator operatively connected to electrical connectors extending longitudinally from a proximal end of the catheter to the actuator;
   transmitting signals from the electrical connectors to the electrically controlled actuator for the adjusting and positioning of the medical device;
   controlling the one or more connections with the actuator to position the medical device;
   attaching the medical device to tissue while the connections are still connected with the medical device;

adjusting the medical device after the medical device has been attached to tissue;

deploying the medical device; and detaching the one or more connections to separate the electrically controlled actuator and the medical device after the medical device has been deployed and positioned at the intended location in the patient.

14. The method according to claim 13, further comprising sending the signals to the electrically-controlled actuator by a control box operatively connected to the electrical connectors at the proximal end of the catheter.

15. The method according to claim 13, wherein positioning the medical device by the electrically-controlled actuator further comprises positioning the medical device by linear movement, rotational movement, inch-worm actuation, rack-and-pinion actuation, a clutch mechanism, or complex displacements, or combinations thereof.

16. The method according to claim 13, further comprising detecting actuation of the one or more connections from the electrically-controlled actuator by a sensor, such that a control box receives feedback to coordinate deployment of the medical device.

17. The method according to claim 14, further comprising positioning the electrically-controlled actuator in response to receiving the signals from the control box.

18. A deployment system, comprising:

a catheter having a distal end with a lumen defined therein sized to receive a deployable medical device therein, and a proximal end;

an electrically controlled actuator mounted and supported on an area on the interior of the lumen in the distal end of the catheter configured to support the actuator with the actuator contacting the area of the catheter; and one or more connections coupled between the electrically controlled actuator and the deployable medical device disposed within the lumen defined in the distal end of the catheter, wherein the connections are controllable by the actuator to adjust the position the deployable medical device.

19. The deployment system according to claim 18, further comprising electrical connectors extending through the catheter to be coupled to the actuator mounted within the distal end of the catheter to transmit signals to the actuator to move the medical device with respect to the actuator while the medical device is coupled with the one or more connections.

20. The deployment system according to claim 18, wherein the wall of the catheter at the distal end thereof includes a reinforced area configured to support the actuator during deployment of the medical device.

* * * * *